United States Patent [19]

Friedrich et al.

[11] 4,026,800
[45] May 31, 1977

[54] DIALYSIS APPARATUS

[75] Inventors: Richard A. Friedrich, Brighton; Robert L. MacNeill, Newburyport, both of Mass.

[73] Assignee: National Medical Care, Inc., Boston, Mass.

[22] Filed: Sept. 30, 1974

[21] Appl. No.: 510,586

Related U.S. Application Data

[63] Continuation-in-part of Ser. No. 462,411, April 19, 1974, abandoned.

[52] U.S. Cl. .............................. 210/87; 210/130; 210/137; 210/197; 210/321 B
[51] Int. Cl.² .................................. B01D 31/00
[58] Field of Search ............ 210/22, 321, 87, 130, 210/197

[56] References Cited

UNITED STATES PATENTS

| | | | |
|---|---|---|---|
| 3,484,369 | 12/1969 | Dubbeleer | 210/321 X |
| 3,528,550 | 4/1970 | Cappelen, Jr. | 210/321 X |
| 3,598,727 | 8/1971 | Willock | 210/321 K X |
| 3,669,878 | 6/1972 | Marantz et al. | 210/22 |
| 3,722,680 | 3/1973 | Smith | 210/321 X |
| 3,880,759 | 4/1975 | Van Assendelft | 210/194 |

*Primary Examiner*—Frank A. Spear, Jr.
*Attorney, Agent, or Firm*—Wolf, Greenfield & Sacks

[57] ABSTRACT

A dialysis module for use with a variety of single pass or single pass-recirculating artificial kidney dialyzers as desired. The apparatus has quick disconnects to allow attachment of a single pass kidney dialyzer or blocking off of a portion of a fluid conduit when a coil dialyzer is used so that a single housing can be used to provide two entirely different modes of operation as selected. A clear canister preferably forms a part of the dialysis flow path in both modes of operation to enable rapid detection of blood leaks in either mode of operation. An aspirator is associated with a recirculating pump to provide negative pressure to dialysate in the flow path when a single pass dialyzer is used while only the recirculating pump is necessary during single pass-recirculating dialysis.

12 Claims, 4 Drawing Figures

DIALYSIS APPARATUS

RELATED APPLICATIONS

This application is a continuation-in-part of our copending U.S. patent application Ser. No. 462,411 filed Apr. 19, 1974, now abandoned.

BACKGROUND OF THE INVENTION

Dialysis has come into widespread use as a mode of treatment for persons having kidney failure. As is known, blood from a patient is passed through a dialyzer and the blood cleansed of harmful ingredients by dialysis through a membrane about which is established a flow of conventional dialysate fluids. The apparatus for mounting conventional artificial kidneys or dialyzers and providing dialysate flow about one side of the dialysis membrane, is normally specifically constructed with a view toward the particular type of dialyzer to be used. This creates a problem when only a single apparatus is available and the treatment necessarily requires the use of a dialyzer different from that which the specific apparatus is capable of handling. This problem has been overcome by use of a dialysis module in accordance with the teaching of our copending continuation-in-part application Ser. No. 462,411. This application provides an improvement over the structure disclosed in said continuation-in-part application.

The most common kidney dialyzers are of one of two basic types. A first type is known as the single pass-recirculating dialyzer. Coil kidney dialyzers are often used in single pass-recirculating mode or systems such as the Ultraflow II dialyzer produced by Travenol Laboratories, Inc. of Morton Grove, Ill. Such dialyzers require high dialysate flow rates through the system, as for example, in excess of 15 liters per minute with the major portion being recirculating flow and another portion being original flow of fresh dialysate. No control over pressure of the dialysate is necessary in such apparatus and the dialyzer is open to atmospheric pressure. In a second type of artificial kidney dialyzer, capillary or parallel flow membranes are provided. In such dialyzers, known as single pass dialyzers, the dialysate flows directly through parallel paths in a single pass about the membranes with no recirculation of the dialysate. Flow rates of from 100cc to 1 liter per minute are often used. Such systems are closed to the atmosphere and pressure control of the dialysate in the dialyzer is used to provide desired pressure. In the single pass type of artificial kidney dialyzers, conventional equipment does not normally provide for visual checking to determine whether or not blood has passed through the dialysis membrane and often, complicated blood leakage detecting devices are used for this purpose. It is important to detect blood leakage to prevent contamination of the system and loss of blood to the patient.

Although it is desirable to have a single dialysis apparatus which could accommodate all types of artificial kidney dialyzers and particularly all commonly commercially used types, no such single apparatus is generally available for use except for the type of apparatus described in our copending continuation-in-part application. This apparatus uses a positive displacement pump to provide negative pressures to produce flow in single pass dialysis. While such pumps are useful, cost, size and operational life factors cause some limits to usage.

SUMMARY OF THE INVENTION

It is an important object of this invention to provide a dialysis apparatus for use with a variety of artificial kidney dialyzers including single pass or single pass-recirculating dialyzers.

Still another object of this invention is to provide a dialysis apparatus in accordance with the preceding object which enables ease of selection for use with a single pass dialyzer or a single pass-recirculating dialyzer.

Still another object of this invention is provide a dialysis apparatus in accordance with the preceding objects which is highly efficient and safe for use over long operating life spans in conventional dialysis procedures.

Still another object of this invention is to provide a dialysis apparatus in accordance with the preceding objects which apparatus has an aspirator or venturi means acting in conjunction with a recirculating pump to provide negative pressure for use during single pass dialysis while allowing use of the recirculating pump function alone during single pass-recirculating dialysis.

According to the invention, a dialysis apparatus has a dialysate flow path and a dialysate recirculating pump in said flow path. A venturi means is associated with the pump and positioned at a first point in the flow path. The venturi means provides negative pressure to dialysate at a second portion in the flow path when the recirculating pump is operated to pump dialysate. Preferably the dialysate apparatus permits selective use with single pass or single pass-recirculating artificial kidney dialyzers. A single housing preferably mounts a two mode system for use with either type of dialyzer. Preferably a dialysate canister is open to the atmosphere and carries a dialysate overflow pipe for limiting a level of dialysate in the canister. A dialysate flow conduit has a first inlet for connection to a source of fresh dialysate fluid and an outlet opening to the canister. A mounting opening is provided in the canister for mechanically mounting an artificial kidney dialyzer therein for use in single pass recirculating dialysis. A recirculating pump means has a conduit interconnecting one portion of the canister with the mounting opening for permitting dialysate recirculation therethrough. A first shunt dialysis conduit is connected to the flow conduit at a first point intermediate the canister opening and the first inlet. The first shunt dialysis conduit terminates at a first shunt connector. A second shunt connector is spaced from the first shunt connector. A second shunt dialysis conduit leads from the second shunt connector to a venturi means at the outlet of the recirculating pump so that the recirculating pump provides a vacuum which in turn creates a negative pressure during single pass dialysis. The second shunt dialysis conduit is interconnected with a pressure regulating valve and pressure regulating conduit preferably in turn connected to the outlet of the recirculating pump or the canister.

It is an important feature of the dialysis apparatus of this invention that it can be used with either a single pass or single pass-recirculating kidney dialyzer. A wide variety of conventional commercially available dialyzers can be interchangeably used with the apparatus of this invention. Negative pressure can be obtained in required amounts at reasonable cost. The size of the apparatus can be compact and the use of the aspirator and recirculating pump to provide negative pressure gives long operating life spans. Operation is quiet since negative pressure is produced without any additional pumping means. In the preferred embodiment, since the canister used is in the dialysate flow path in both single pass and single pass-recirculating modes of operation, visual inspection is possible to detect blood leak loss of at least as low as less than 5 cc in 6 hour's time. Positive pressure relief is preferably provided by a valve which prevents the dialyzer from being subjected to dangerous levels of positive pressure. The apparatus can be constructed with substantially conventional components and provides high safety with good reliability in use.

BRIEF DESCRIPTION OF THE DRAWINGS

The above and other objects, advantages and features of the present invention will be better understood from the following specification when read in connection with the accompanying drawings in which.

DESCRIPTION OF PREFERRED EMBODIMENTS

Figure 1:
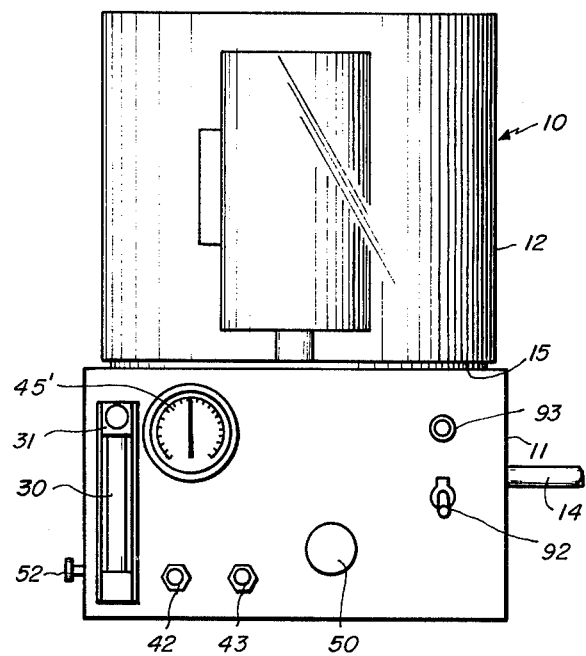
FIG. 1 is a preferred view of a preferred embodiment of a dialysis apparatus in accordance with this invention.

With reference now to the drawings and more particularly FIG. 1, a preferred embodiment of a dialysis model or apparatus is illustrated generally at 10. A housing 11 carries a top mounted clear dialysate canister 12 preferably formed of a clear, transparent plastic material such as polystyrene or polycarbonate and is open to the atmosphere at its top. A dialysate quick disconnect 13 (FIG. 2 and 3) is mounted on the rear of the housing as is a quick disconnect (not shown) for a drain conduit 14.

The dialysis apparatus 10 is designed for use with a central station fresh dialysate delivery system of any conventional type. For example, a central system can be used which provides dialysate supplies to several modules such as 10, to enable dialysate flow for carrying out blood dialysis on a plurality of patients at a plurality of stations.

The dialysate flow system is preferably formed of conventional plastic piping such as polyvinyl chloride tubing although stainless steel or other materials can be used. The dialysate flow system is carried substantially within the housing with the dialysate canister 12 preferably mounted at the top of the housing. The canister 12 is preferably cylindrical in form and has a bottom wall 15 resting over a top wall of the housing 11. An overflow pipe 16 extends up into the canister and is interconnected through the wall 15 to a drain outlet 14 as by conventional fittings not shown. A dialysate flow conduit 20 is connected at one end to a self-sealing, quick disconnect 13 for connection with a source of fresh liquid dialysate as from a central dialysate supply as known in the art. An outlet opening 21 of the dialysate conduit 20 opens to the inlet of a recirculating pump 24 and a short pipe leading from the chamber 22 of the canister. Opening 21 can lead directly into the canister although it is preferably at the inlet of the recirculating pump 24. Thus, the outlet opening 21 passes dialysate to the canister although the dialysate may first pass through the recirculating pump. A mounting opening 23 is also provided in the bottom wall 15 of the canister and enables plug in detachable mounting of conventional recirculating dialyzers directly in the chamber 22. The mounting opening has a conventional rubber grommet means or other joint structure to enable ease of connecting and disconnecting the dialyzer when required. The recirculating pump 24 provided in a recirculating pump conduit 25 connects a portion 26 of the canister with the mounting opening 23 permitting dialysate recirculation from the chamber 22 and through a dialyzer such as 91 (FIG. 3) mounted in the chamber 22. A conventional flow meter 30 is positioned in conduit 20 for controlling flow of fresh dialysate. The flow meter can for example be a model VFA flow meter produced by Dwyer Instruments, Inc. of Michigan City, Ind. A dialysate metering valve 31 is preferably integral with the flow meter 30 and regulates the rate of flow through conduit 20 of the fresh dialysate. Metering valve 31 is of a conventional type and is preferably hand adjustable although a fixed metering valve can be used if desired. A pressure relief check valve 32 is provided in the dialysate flow conduit 20 which prevents flow through conduit 20 toward the quick disconnect 13 in all modes of operation and allows a small flow in a direction away from the quick disconnect due to vacuum created in the upper portion of line 20 by the recirculating pump 24 during single pass operation. The check valve of the preferred embodiment is a model ss-4cp2-1 pressure relief valve produced by Nupro Company of Cleveland, Ohio. The check valve 32 acts as a safety valve in that if other pathways through the system are clogged as by kinked lines or backups, dialysate flow will pass through the check valve toward the canister at pressures above 1 psi. Thus flow continues although dialysis stops and the single pass dialyzer is not subjected to excessive dialysate pressure. During single pass-recirculating dialysis, all flow is preferably through valve 32 and line 20.

A first shunt dialysate conduit 40 forms a part of the flow path and is connected to the flow conduit 20 at a first point 41 intermediate the canister opening 21 and the quick disconnect 13. The conduit 40 leads to a self-sealing, quick disconnect or shunt connector 42 and carries a dialysate pressure gauge 45' to enable readout of dialysate pressure. The dialysate pressure gauge 45' can be mounted in other portions of the system if desired. The pressure gauge can be a conventional pressure gauge such as a model 2 1/2 109SXMS Ascroft produced by Dresser Industries, Inc. of Stratford, Conn. A second shunt connector in the form of a self-sealing quick disconnect 43 is preferably positioned on the front panel of the apparatus 10 and connect with a second shunt dialysis conduit 44 which forms a part of the dialysate flow path during single pass dialysis. Conduit 44 passes a node 45 and has a passageway 46 leading to an aspirator 47 at an aspirator port 48.

Passing from the node 45 where mixing of recirculating and original dialysate occurs is a second conduit 49 regulated by a pressure regulating valve 50 which can be a hand operated flow valve. Passageway 49 preferably passes to the outlet of the recirculating pump as at 51 but prior to the venturi portion of the aspirator 47. The conduit 49 is also connected to the drain tube 14 through a drain valve 52 to allow flushing of the system when desired.

The aspirator in the preferred embodiment is a model 1800 aspirator produced by Clay Adams Division of Becton Dickinson Company, Parsippany, N.J.

The aspirator 47 is the significant portion of the improvement of this invention in that it is used in cooperation with the recirculating pump to provide negative pressure when a single pass dialyzer such as 61 is employed in the system for single pass dialysis. Aspirators have been used before to provide pressure in dialysis systems. However, such aspirators normally are run from water mains as their source of energy to enable them to produce vacuums in single pass dialysis. The present system eliminates this need for large amounts of water because the effluent dialysate itself from the single pass kidney is used as the powering source in conjunction with the recirculating pump as the driving power. The pumps used can be any fluid recirculating pump preferably capable of producing a flow of at least 10 gallons per minute at 12 psi. In the preferred embodiment the recirculating pump is a model 4MD Little Giant Corporation, Oklahoma City, Okla.

The aspirator is effectively a venturi means and creates a vacuum at the port 48 through well-known principles when the recirculating pump is turned on and recirculation of fluid occurs through the pump. Valve 50 is used as a regulating means to regulate the amount of negative pressure produced in the flow path 44. When the valve is fully closed, maximum negative pressure is produced and conversely fully opened, minimum negative pressure is produced. The values of pressure in the preferred embodiment at 500 cc dialysate flow rate run from about 0 to about −600 millimeters of mercury.

The system is further provided with one way check valves 62, 63 and 64 which act as safety devices to prevent backflow of used dialysate fluid or disinfecting fluid during cleaning of the device. Backflow of such materials into the central dialysate system can be a serious problem although the check valves in no way are essential to the operation of the systems of this invention.

The quick disconnects 13, 42 and 43 are of conventional design and allow plugging in of conduiting whereupon the path is open and when the conduiting is unplugged, liquid leaks are prevented at fluid pressures normally encountered in the range of from −200 to 600 mm of Hg or higher. Quick disconnects such as model 294-PSS connects produced by Imperial Eastman Corp. of Chicago, Ill. are suitable for use. Other connection means can be used in place of the quick disconnects. For example, screw in couplings and manually operable turn valves can be used. The conduiting used in the preferred embodiment is preferably ¼ inch inside diameter conduiting except for conduits 25 and 14 which are ¾ inch inside diameter conduits.

Figure 2:
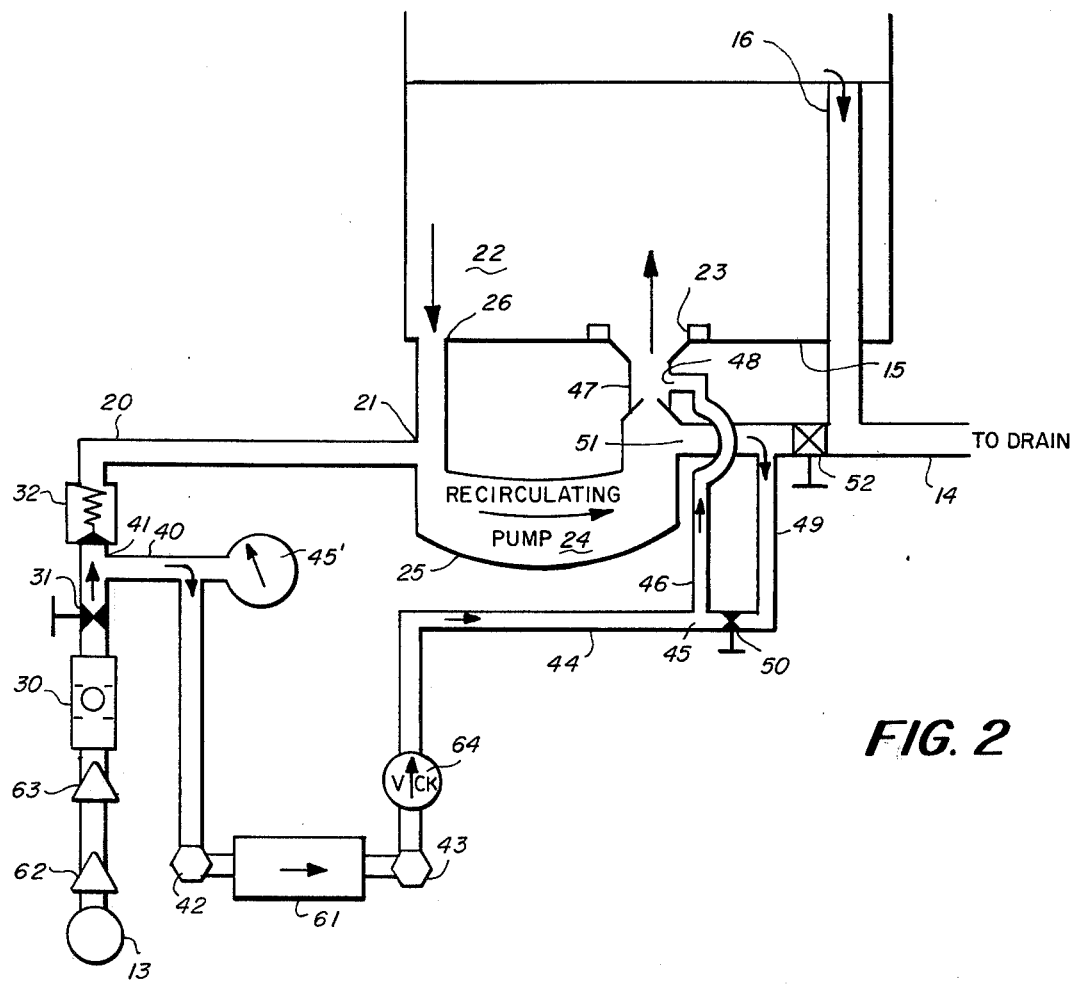
FIG. 2 is a semidiagrammatic drawing of the dialysis flow path system therein when used in a single pass mode.

In the single pass mode of operation, the dialysate inlet of the single pass dialyzer 61 as shown in FIG. 2 is connected to quick disconnect 42 and the outlet connected to quick disconnect 43. The recirculating pump 24 is turned on by electrical switch 92 which causes lighting of an indicator light 93 on the front panel of the machine. The blood flow path through the dialyzer is not shown in the drawings but is as conventional in the art with blood passed from and to the patient flowing in the membranes of the dialyzer. Fresh dialysate from the central delivery system is provided through quick disconnect 13 and flows through the flow meter 30. At the outlet of the flow meter it passes through the dialysate metering valve 31 whih regulates the rate of flow. The dialysate is then conducted to the self-sealing quick disconnect 42 with dialysate pressure gauge 45' measuring dialysate pressure at this point in the system. The dialysate is then passed to the single pass kidney dialyzer diagrammatically shown at 61, to the inlet of the negative pressure applying system which starts at the node 45. The first bit of dialysate flow acts to fill the canister 12 to the level of the overflow pipe 16 or at least to a level sufficiently high to allow recycling through the recirculating pump 24. The valve 50 can be regulated to allow negative pressure of from 0 to −600 mm Hg. Degrees of negative pressure less than the maximum are produced by opening the dialysate pressure regulating valve 50 as desired. The drain valve 52 remains closed during the single pass mode of operation and no dialysate passes in the flow path 20 past the pressure relief valve 32 unless a kink in the system develops and pressure above 50 mm Hg builds up whereupon flow directly to the canister, through line 20, occurs preventing buildup of unwanted dialysate pressure in the system. Possible blood leaks from the artificial kidney can be detected by observation of turbidity of the effluent dialysate in the clear, transparent canister 12.

Figure 3:
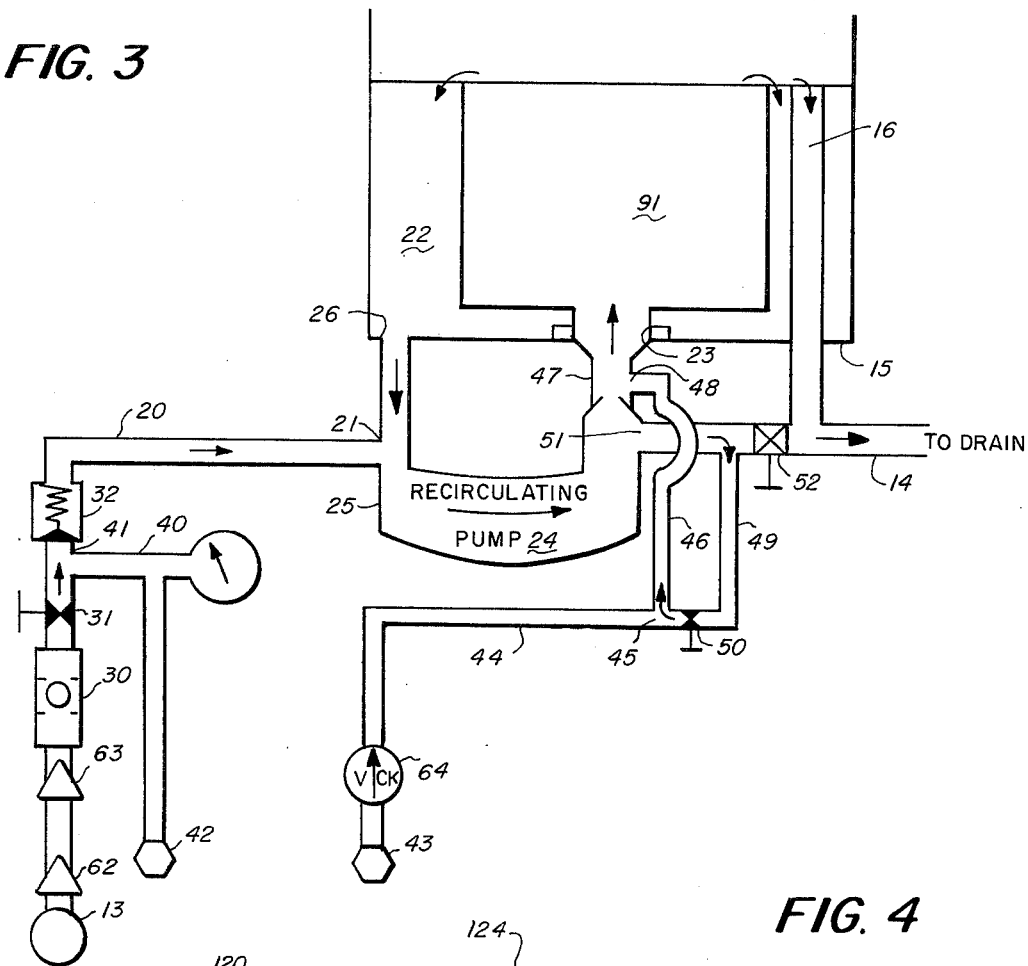
FIG. 3 is a semidiagrammatic drawing of the dialysate flow path system therein when used in a single pass-recirculating mode of operation.

In the recirculating mode of operation shown in FIG. 3, the single pass dialyzer 61 is removed and a plug (not shown) is inserted in quick disconnect 43 to positively fully seal it even if a vacuum in line 44 exceeds the spring pressure normally applied to close the quick disconnect. A single pass recirculating dialyzer such as coil dialyzer 91 is inserted in the opening 23 at the center of the canister as known in the art. Flow of the dialysate from the central dialysate delivery system preferably passes directly through line 20 to the canister 10. In some cases, a shunt pipe can be connected between quick disconnects 42 and 43 with flow passing through line 44 and not line 20 during recirculating dialysis although this is not preferred. The recirculating pump is turned on and in the preferred embodiment, the portion 44 is out of the dialysate flow path during recirculation using a coil dialyzer.

Dialysate flows into the recirculating system through the pump 24 and fills the clear canister. The dialysate content of the canister may be for example 8 liters and the overflow 16 determines the top level of the dialysate flow. In this mode of operation, fluid flow is indicated by the arrows shown in FIG. 3 with an acceptable low level of waste product in the dialysate maintained in the recirculating volume by the constant addition of fresh fluid.

The unit 10 can have a base housing dimension with a length of 14 inches, a width of 14 inches and a height of 7 inches with the canister having a diameter of 12 inches and a height of 10 inches. Thus a highly compact unit can be provided. All necessary controls for dialysate flow are accessible from the front panel of the unit as shown in FIG. 1. Switch 92 activates the recirculating pump 24 which is used in both the single pass and single pass-recirculating modes of operation. The quick disconnects 42 and 43 are readily accessible from the front of the machine for connection of a shunt line or preferably a single pass kidney 61. Conventional connections are made within the machine to provide for suitable electrical wiring to the recirculating pump along with the pump indicator light 93. The electrical circuit is preferably such that the electrical components of the machine can be activated through conventional line currents such as 120 volt 60 cycle current.

The preferred recirculating pump is preferably a sealless orbital-magnetic driven centrifugal pump with sufficient capacity to power the aspirator at the required level of performance. It is this pump acting with the aspirator which gives an operating life far in excess of prior systems of this type such as those employing positive displacement pumps. Moreover the recirculating pump has a dual function in that it acts to activate the aspirator in single pass operation while it acts to cause recirculation in single pass-recirculating dialysis. Either single pass or single pass-recirculating modes of operation allow use of 200 liters of dialysate in a 6 hour period for the dialysate flow through the machine during a normal treatment period for a patient. In the single pass-recirculating mode of operation with the tank 12 holding an 8 liter volume of dialysate, an excess of 15 liters per minute can be recirculated with about 500 cc per minute of fresh dialysate added permitting a high dialysis flow rate through the system. Flow rates can be from 200 cc to 1 liter per minute if desired. No control over dialysate pressure is maintained since the system is open to the atmosphere. In the single pass mode of operation using a parallel flow dialyzer, a similar flow rate can be maintained which is preferably about 500 cc per minute. The tank again holds 8 liters mainly to allow visual inspection.

While specific embodiments of the present invention have been shown and described, it will be obvious that many modifications are possible. For example, the particular materials of the conducting, canister and the like can vary. The particular disconnects used as well as the meters and pumps can be varied as known in the art. In all cases, the recirculating pump used for coil dialysis is also used to power an aspirator and thus provide negative pressure during single pass operation.

The degree of negative pressure can be regulated in other ways than the regulation valve 50 shown. For example, the pressure regulating valve 50 can be placed directly in conduit 46. The conduit portion 49 can have its outlet 51 within the canister or at any other part of the drain tubing or to the outside if desired without affecting the pressure regulating capacity of the valve 50.

Although it is preferred to use the combination of a recirculating pump and aspirator to produce negative pressure in connection with a system of the type disclosed in our copending application Ser. No. 462,411 filed in the U.S. Patent Office Apr. 19, 1974 entitled DIALYSIS APPARATUS, which is incorporated by reference herein, this combination has advantages in other dialysis apparatus. For example, conventional coil dialysis modules and apparatus adopted only for use as single pass-recirculating modules can easily be adapted for use with single pass dialyzers in accordance with the principles of this invention.

Figure 4:
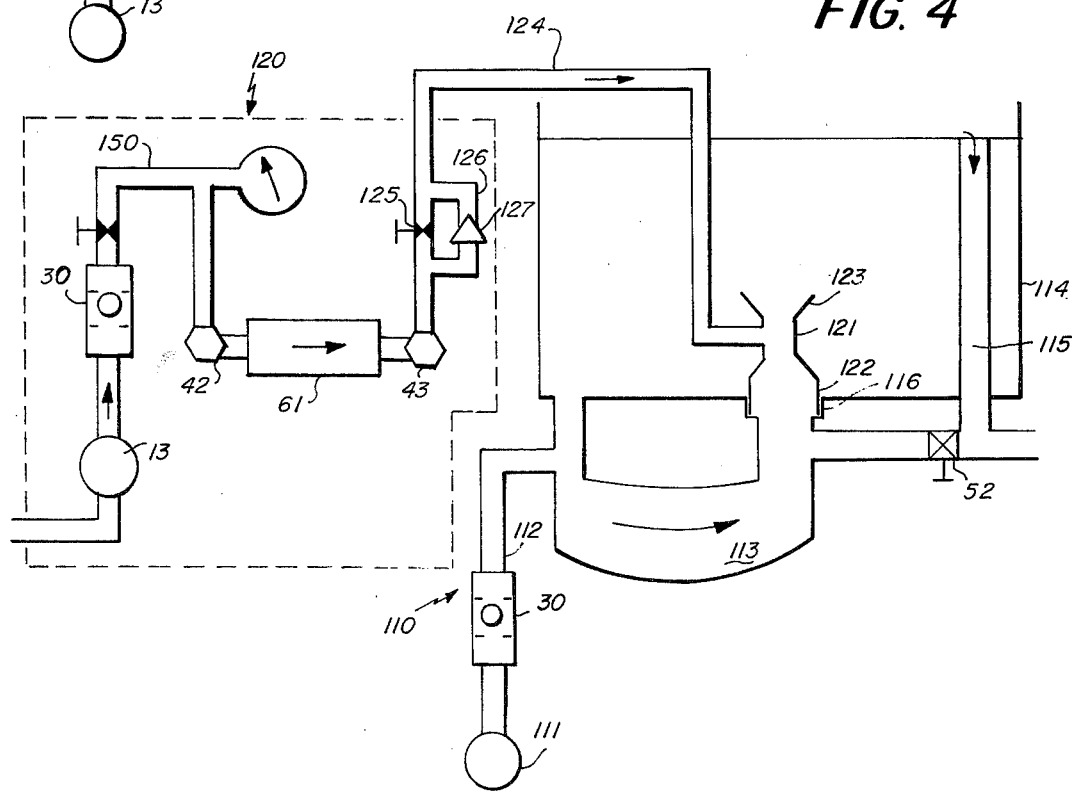
FIG. 4 is a diagrammatic showing of an alternate embodiment of the system in accordance with the present invention.

For example, as shown in FIG. 4, a plug in venturi unit is shown for rapidly and inexpensively converting a conventional coil dialyzer module to one also suitable for single pass operation. In this embodiment, a conventional coil dialysis apparatus, of any one of a number of known types, is shown diagrammatically at 110 having a dialysate inlet 111, suitable conduiting 112, a recirculating pump 113, a canister 114 with conventional overflow pipe 115 and a neck portion 116 for attachment of a conventional coil dialyzer. A separate unit 120 is shown comprising an aspirator 121 having an end 122 adapted to be plugged into the opening 116 in the same manner as the end of a coil dialyzer. A second end of the aspirator 123 permits flow of dialysate fluid therefrom. A conduit 124 extends back to a pressure adjusting gate valve 125 with a shunt conduit 126 carrying a one-way check valve 127. A quick disconnect such as 43 previously described allows connection of a single pass dialyzer such as 61 previously described. A quick disconnect 42 as previously described is connected to a conduit 150 which is in turn connected to a quick disconnect 13 as previously described along with suitable check valves and flow meters as previously described. This portion of the unit is encased in a housing indicated by the dotted lines shown at 120. Using this system the recirculating pump 113 of a conventional coil dialyzer along with its tank can be used for single pass dialysis by the mere plug in of a simple module to again form the combination of a venturi means and driving recirculating pump. In some cases, the venturi means can be plugged into the inlet of the pump although the outlet is preferred. In all cases, the recirculating pump, pumps dialysate to provide the driving energy and the venturi means is suitably associated with it to provide the required driving means to dialysate coming from the single pass dialyzer.

What is claimed is:

1. In a dialysis apparatus having a dialysate flow path comprising a first point and a second point, a dialysate recirculating pump in said path for circulating dialysate in said apparatus,
    the improvement comprising,
    a venturi means operatively interconnected with said pump and powered by said pump, with said venturi means being positioned at the first point in said flow path,
    said venturi means providing a negative pressure to cause desired flow of dialysate and reduced pressure in the dialysate at the second point in said flow path.

2. The improvement of claim 1 and further comprising said venturi means comprising a restricted passageway adjacent an outlet of said recirculating pump,
    an aspirator passageway opening into said restricted passageway and means for adjusting the negative pressure provided to said dialysate to cause reduced pressure and desired flow thereof through a single pass dialyzer.

3. The improvement of claim 1 and further comprising,
    means for adjusting said negative pressure,
    said means for adjusting comprising a flow restricting regulating valve and a passageway connected to said flow path.

4. A dialysis conversion system for converting a conventional single pass-recirculating coil dialysis apparatus for use with a single pass dialyzer,
    said conversion apparatus comprising a venturi means having connection means for connection with a recirculating pump carried in said coil dialysis apparatus,
    said venturi means being interconnected with conduiting to pressure regulating means and dialysate inlet means having means for connection of a single pass dialyzer therein so that said venturi means acts to provide negative pressure to cause desired flow and reduced pressure in dialysate passing through said dialyzer.

5. A dialysis apparatus for selective use with single pass or single pass-recirculating artificial kidney dialyzers to provide for dialysate flow, said apparatus comprising, a housing, a dialysate canister open to the atmosphere and carrying a dialysate overflow means for limiting a level of dialysate in said canister, a dialysate flow conduit having a first inlet for connection to a source of fresh dialysate and an outlet opening for passing dialysate to said canister, a mounting in said canister for detachably mechanically mounting an artificial kidney dialyzer therein, recirculating pump means having a conduit interconnecting one portion of the canister with a second portion at said mounting for permitting dialysate recirculation therethrough, aspirator means interconnected with said recirculating pumps means, said aspirator means being connected to a shunt passageway leading to a first shunt connector, a second shunt connector interconnected with said first-mentioned flow conduit, whereby operation of said recirculating pump provides negative pressure to dialysate in said shunt conduit when a single pass dialyzer is interconnected between said shunt connectors yet allows recirculation of dialysate in said canister when fluid flow through said second shunt conduit is blocked off while fluid flow through said first-mentioned flow conduit occurs.

6. A dialysis apparatus in accordance with claim 5 wherein said first and second shunt connectors are quick disconnect connectors.

7. A dialysis apparatus in accordance with claim 5 wherein said shunt passageway has a negative pressure regulating conduit attached to a node thereof with a pressure regulating valve located in said pressure regulating conduit, whereby said valve permits adjustment of negative pressure produced by said aspirator means.

8. A dialysis apparatus in accordance with claim 7 and further comprising said pressure regulating conduit opening to a portion of said dialysis apparatus carrying dialysate.

9. A dialysis apparatus in accordance with claim 8 wherein said aspirator means is interconnected with said recirculating pump at the outlet thereof before said mounting for detachably mechanically mounting an artificial kidney dialyzer.

10. A dialysis apparatus in accordance with claim 5 wherein said canister is a transparent canister allowing detection of blood leaks to dialysate contained therein.

11. A dialysis apparatus in accordance with claim 9 wherein said canister is a transparent canister allowing detection of blood leaks to dialysate contained therein.

12. A dialysis apparatus in accordance with claim 9 wherein, said dialysate flow conduit carries a flow meter and pressure relief valve therein and said second shunt connector is connected to said flow conduit at a point intermediate said pressure relief valve and said first inlet.

* * * * *